(12) United States Patent
Gammons

(10) Patent No.: US 6,709,447 B1
(45) Date of Patent: Mar. 23, 2004

(54) INFLATABLE THERMAL BLANKET

(75) Inventor: Clifford Eugene Gammons, Loudon, TN (US)

(73) Assignee: Adroit Development, Inc., Loudon, TN (US)

(*) Notice: Subject to any disclaimer, the term of this patent is extended or adjusted under 35 U.S.C. 154(b) by 0 days.

(21) Appl. No.: 10/300,405

(22) Filed: Nov. 20, 2002

(51) Int. Cl.[7] .................................................. A61F 7/00
(52) U.S. Cl. ....................................... 607/104; 607/107
(58) Field of Search ....................... 607/96, 104, 107, 607/108–112

(56) References Cited

U.S. PATENT DOCUMENTS

| | | |
|---|---|---|
| 1,777,982 A | 10/1930 | Popp |
| 2,093,834 A | 9/1937 | Gaugler |
| 3,653,083 A | 4/1972 | Lapidus |
| 4,347,633 A | 9/1982 | Gammons et al. |
| 4,572,188 A | 2/1986 | Augustine et al. |
| 4,660,388 A | 4/1987 | Greene, Jr. |
| 4,777,802 A | 10/1988 | Feher |
| 5,106,373 A | 4/1992 | Augustine et al. |
| 5,165,400 A | 11/1992 | Berke |
| 5,184,612 A | 2/1993 | Augustine |
| 5,300,101 A | 4/1994 | Augustine et al. |
| 5,300,102 A | 4/1994 | Augustine et al. |
| 5,304,213 A | 4/1994 | Berke et al. |
| 5,324,320 A | 6/1994 | Augustine et al. |
| 5,336,250 A | 8/1994 | Augustine |
| 5,350,417 A | 9/1994 | Augustine |
| 5,405,371 A | 4/1995 | Augustine et al. |
| 5,545,194 A | 8/1996 | Augustine |
| 5,655,237 A * | 8/1997 | Suzuki et al. ............... 5/502 |
| 5,674,269 A | 10/1997 | Augustine |
| 5,824,025 A * | 10/1998 | Augustine ............... 607/107 |
| 5,860,292 A | 1/1999 | Augustine et al. |
| 6,102,936 A | 8/2000 | Augustine et al. |
| 6,176,870 B1 * | 1/2001 | Augustine ............... 607/107 |
| 6,210,428 B1 | 4/2001 | Augustine et al. |
| 6,228,107 B1 | 5/2001 | Arnold et al. |
| 6,487,871 B1 * | 12/2002 | Augustine et al. ......... 62/259.3 |

FOREIGN PATENT DOCUMENTS

| | | |
|---|---|---|
| GB | 716746 | 10/1954 |
| GB | 1334935 | 10/1973 |
| GB | 1566207 | 4/1980 |
| WO | PCT/US85/00071 | 8/1985 |

* cited by examiner

*Primary Examiner*—Roy D. Gibson
(74) *Attorney, Agent, or Firm*—Pitts & Brittain, P.C.

(57) ABSTRACT

An inflatable thermal blanket (10) for providing a conditioned gas to at least a portion of the body of a human or other animal. The thermal blanket (10) includes an inflatable portion (18) for receiving the conditioned gas under pressure and for being positioned over a portion of the body of the user. The inflatable portion (18) is defined by a base sheet (12) adapted for communicating the conditioned gas to a portion of the body of the user, and an outer sheet (14). The inflatable portion (18) also includes an inlet port (20) for placing the inflatable portion in fluid communication with a source of conditioned gas. The inflatable portion (18) also defines at least one outer channel (30) communicating with the inlet port (20) and at least one inner channel (32) communicating with the outer channel (30). The inner channel (32) is formed in part by the base sheet (12), and the outer channel (30) is formed at least in part by the outer sheet (14) and a baffle (34) such that the inner channel (32) is disposed between the outer channel (30) and the body of the user, whereby the conditioned gas received through the inlet port (20) is dispersed into the outer channel (30) before being communicated to the inner channel (32).

15 Claims, 10 Drawing Sheets

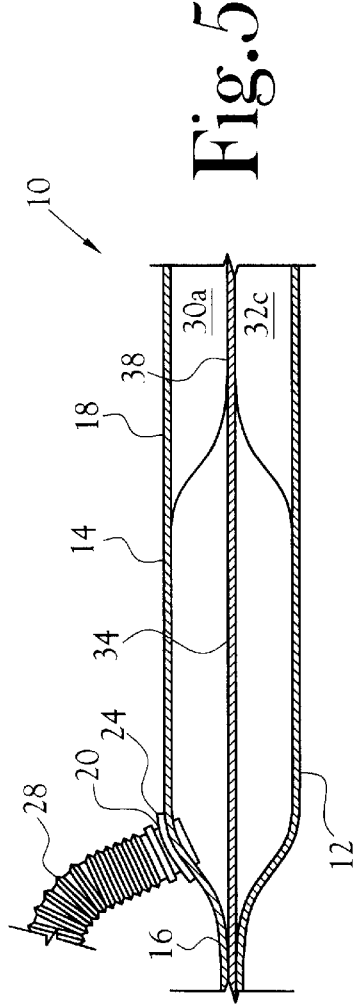
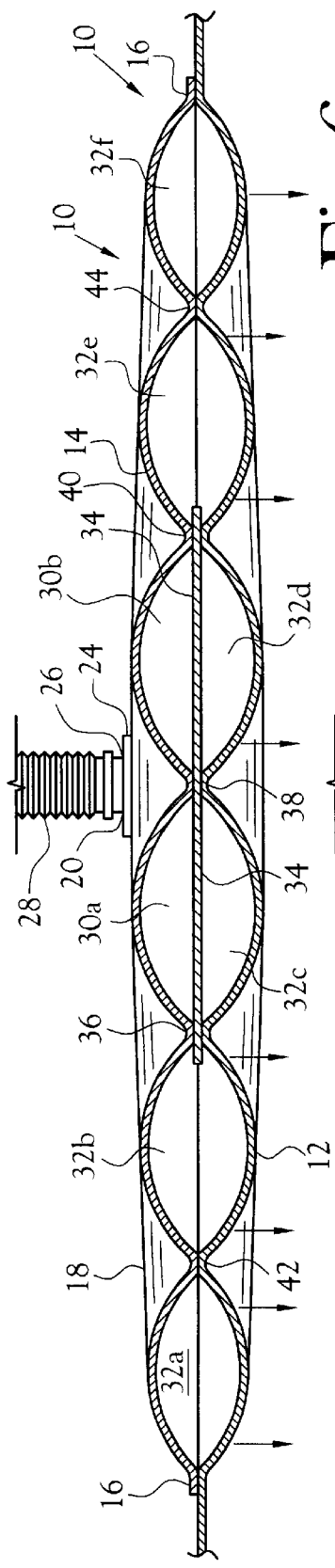
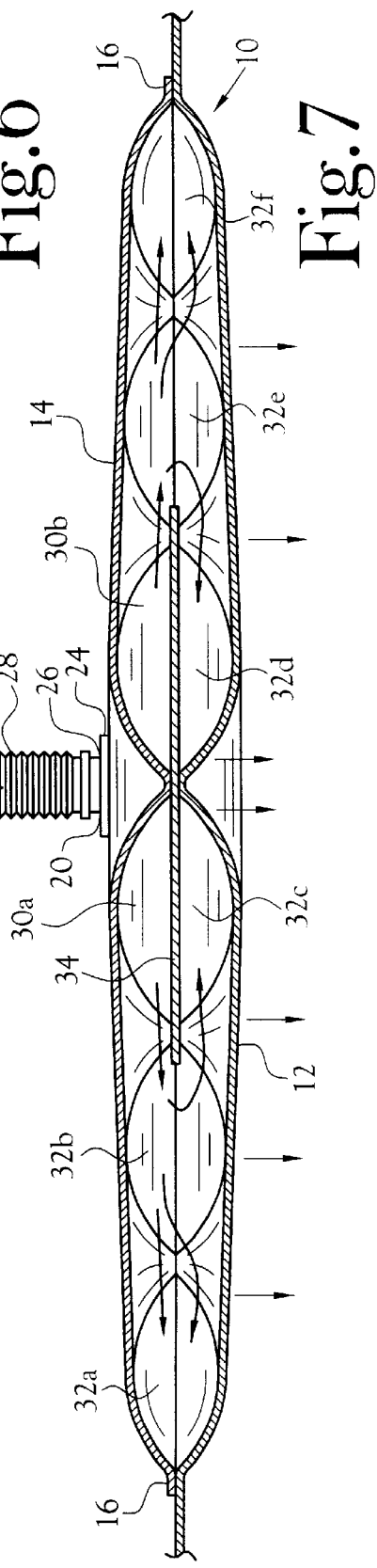

INFLATABLE THERMAL BLANKET

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of Invention

This invention relates to a blanket for covering it least a portion of the body of a human, or other animal, in order to bath the body portion in a conditioned gas. More specifically, the present invention is related to an inflatable thermal blanket for providing a conditioned gas, such as, for example, heated air, to a portion of the body of a user.

2. Description of the Related Art

Inflatable thermal blankets which are used to communicate a conditioned gas, such as heated or cooled air, to a patient are known in the art. Such thermal blankets typically have an inflatable portion provided with an inlet port for placing the inflatable portion in fluid communication with a source of pressurized, conditioned gas such that the inflatable portion can be selectively inflated. The inflatable portion generally has an inner surface which is gas pervious, or which is otherwise adapted to communicate the conditioned gas used to inflate the blanket to the user. Such thermal blankets are often used to treat conditions such as hypothermia, or used to reduce the body temperature of a user in circumstances where the body temperature is inappropriately high. For example, where a patient is being treated for hypothermia, at least a portion of the patient's body is covered with the thermal blanket, and warm air is pumped into the inflatable portion. The warm air used to inflate the inflatable portion is thereafter communicated through the inner surface of the inflatable portion so as to bath the body portion covered by the blanket in warm air. Examples of such thermal blankets are disclosed in U.S. Pat. Nos. 5,184,612; 5,304,213; and 5,324,320. Whereas prior art thermal blankets serve to deliver conditioned air to a patient, the temperature of the air being communicated through the inner surface of the inflatable portion, and the surface temperature of the inner surface, can vary greatly over the area of the inner surface. For example, if heated air is pumped into the inflatable portion through the inlet port, the air within the blanket near the inlet port tends to be substantially higher in temperature than the air within the blanket which is remote from the inlet port. Accordingly, the inner surface of the blanket proximate the inlet port, and the air communicated to the patient through the inner surface of the blanket proximate the inlet port, can be uncomfortably, or damagingly, hot when the blanket is otherwise communicating air of the desired temperature to the patient. Whereas the temperature of the air entering the inlet port can be reduced to avoid uncomfortable, or damaging, hot spots near the inlet port, such a reduction of temperature can compromise the overall effectiveness of the thermal blanket.

Other devices for warming or cooling patients, and/or for communicating conditioned air to a patient, are disclosed in U.S. Pat. Nos. 1,777,982; 2,093,834; 3,653,083; 4,347,633; 4,472,847; 4,572,188; 4,660,388; 4,777,802; 5,106,373; 5,165,400; 5,300,101; 5,300,102; 5,336,250; 5,350,417; 5,405,371; 5,545,194; 5,674,269; 5,860,292; 6,102,936; 6,210,428 B1; and 6,228,107 B1. See also, PCT International Application No. PCT/US85/00071, and British Patent Nos. 716,746; 1 334 935; and 1 566 207.

BRIEF SUMMARY OF THE INVENTION

The present invention provides an inflatable thermal blanket for providing a conditioned gas, such as, for example, heated air, to at least a portion of the body of a human or other animal. The thermal blanket includes an inflatable portion for receiving the conditioned gas under pressure and for being positioned over at least a portion of the body of the user. The inflatable portion is defined by a base sheet which is fabricated of a gas pervious material, or which is otherwise adapted for communicating the conditioned gas to a portion of the body, and defines an outer sheet which is substantially gas impervious. The inflatable portion also includes an inlet port for placing the inflatable portion in fluid communication with a source of conditioned gas, and is constructed so as to define at least one outer channel communicating with the inlet port and one or more inner channels communicating with the outer channel. The inner channels are formed in part by the base sheet such that conditioned gas within the inner channels is communicated through the base sheet to the body of the user. The outer channel is formed at least in part by the outer sheet and an interior wall, or baffle, such that one or more of the inner channels is disposed between the outer channel and the body of the user when the blanket is in use. Accordingly, the conditioned gas that is received through the inlet port is dispersed into the outer channel before being communicated to the inner channel. Thus, the conditioned gas is allowed to disperse, and the temperature of the conditioned gas is allowed to moderate, before it is communicated to the inner channels, thereby reducing temperature variations over the inner surface of the inflatable portion.

BRIEF DESCRIPTION OF THE SEVERAL VIEWS OF THE DRAWINGS

The above-mentioned features of the invention will become more clearly understood from the following detailed description of the invention read together with the drawings in which:

FIG. 5 is a partial side elevation view, in section taken at A—A of FIG. 4, of an inflatable thermal blanket of the present invention;

FIG. 6 is a partial end view, in section taken at B—B of FIG. 4, of an inflatable thermal blanket of the present invention;

FIG. 7 is a partial end view, in section taken at C—C of FIG. 4, of an inflatable thermal blanket of the present invention;

DETAILED DESCRIPTION OF THE INVENTION

Figure 1:
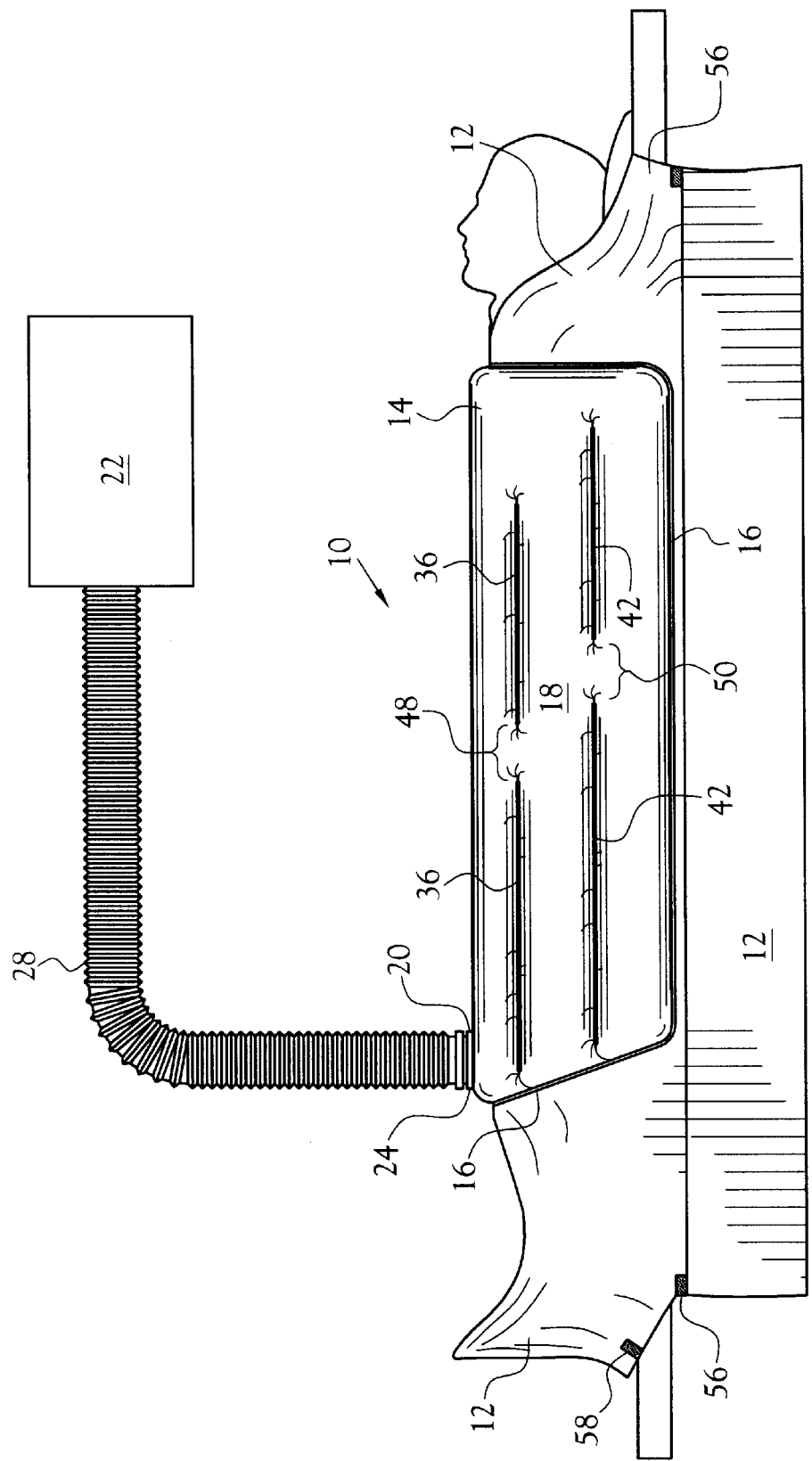
FIG. 1 is a side elevation view of an inflatable thermal blanket of the present invention.
Figure 2:
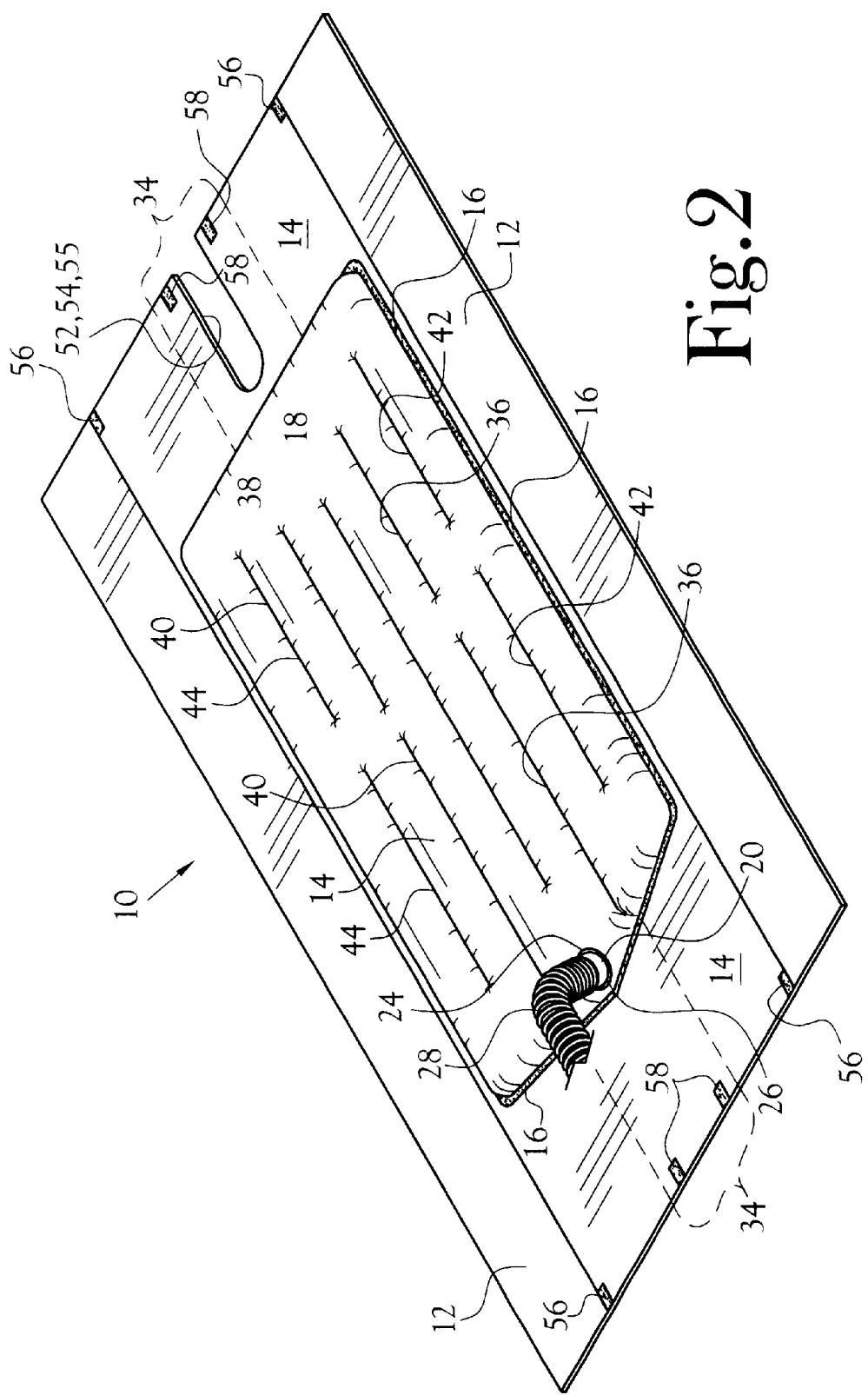
FIG. 2 is a perspective view of an inflatable thermal blanket of the present invention.

An inflatable thermal blanket in accordance with the present invention is illustrated generally at 10 in FIGS. 1–7. The thermal blanket 10 is designed to cover at least a portion of the body of a human, or other animal, and to bath at least a portion of such body with a conditioned gas, such as thermally conditioned air. The thermal blanket 10 is particularly useful in bathing a body portion in air which has been heated to a temperature above normal body temperature in order to treat conditions such as hypothermia. However, it will be understood that gaseous fluids other than air can be used, and in certain applications the gaseous fluid utilized may be delivered to the body portion at a temperature which is at, or lower than, normal body temperature, as in the case where the existing body temperature is abnormally high and cooling is desired.

The thermal blanket 10 includes a first or base sheet 12, at least a portion or portions, of which are pervious to gaseous fluids such as air. Preferably the base sheet 12 is fabricated of a natural, or synthetic, non-woven material through which air under pressure can be communicated. Whereas synthetic materials such as, for example, polyester, can be used, the use of a cellulose or paper based material is preferable where a single use, disposable thermal blanket is desired. It will also be understood from the discussion which follows that the base sheet 12 can be fabricated of a gas impervious material that is provided with openings through which gas can pass, or can be fabricated of a material that is gas pervious in selected areas and otherwise gas impervious.

The thermal blanket 10 also includes a second or outer sheet 14 which is attached to the base sheet 12 along a seam 16 such that the base sheet 12 and the outer sheet 14 define an inflatable portion 18. In this regard, in the preferred embodiment the outer sheet 14 is fabricated of a substantially gas impervious material, such as, for example, a cellulose based sheet material coated with a film of polyethylene or polypropylene. The outer sheet 14 is preferably attached to the base sheet 12 along the seam 16 by heat bonding, but various adhesive or other bonding methods can be used. The outer sheet 14 is provided with an inlet port 20 for placing the inflatable portion 18 in fluid communication with a suitable source of pressurized gas, such as, for example, the heater/blower 22 schematically illustrated in FIG. 1. More specifically, in the preferred embodiment, the inlet port 20 is defined by a reinforcing collar 24 which has an opening 26 for receiving the end of a supply hose 28. As noted above, in one preferred embodiment the outer sheet 14 is fabricated of cellulose based sheet material coated with a film of polyethylene or polypropylene. In this embodiment, the collar 24 is secured to the outer sheet 14 and no opening is made in the outer sheet 14 during manufacture. When the thermal blanket 10 is used, the portion of the outer sheet 14 within the opening 26 is torn to allow the insertion of the end of the hose 28.

As discussed in greater detail below with respect to specific embodiments of the thermal blanket of the present invention, the inflatable portion 18 of the thermal blanket 10, defines at least one outer channel 30, and one or more inner channels 32. The inner channels 32 are formed in part by the base sheet 12 which is disposed proximate the human or animal patient during use of the blanket 10 such that conditioned air within the inflatable portion is communicated through the base sheet 12 toward the patient. The outer channel 30 is formed by the outer sheet 14 and a wall or baffle 34, such that at least one of the inner channels 32 is disposed between the outer channel 30 and the human or animal patient. In this regard, the inlet port 20 communicates with the outer channel 30, and the outer channel 30, in turn, communicates with the inner channels 32 such that as the conditioned gas enters the inflatable portion 18, it passes first into the outer channel 30, and then into the inner channels 32. Where the conditioned gas is, for example, heated air, the heated air entering the inflated portion 18 at the inlet port 20 is allowed to disperse and cool as it travels down the outer channel 30 without the heated air being immediately communicated to the patient. When the heated air is subsequently communicated into the inner channels 32, it is more evenly dispersed and the temperature of the air being communicated to the patient through the base sheet 12 is more consistent over the area of the inner surface of the inflatable portion 18. Consequently, by providing the outer channel 30 to disperse the incoming air before it is communicated to the patient the area of increased temperature proximate the inlet port typical of prior art thermal blankets is avoided. Of course, where the conditioned gas being used is gas which as been cooled below body temperature, the outer channel 30 also facilitates dispersal of the gas into the inner channels 32 such that the temperature of the air being communicated to the patient through the base sheet 12 is more consistent over the area of the inner surface of the inflatable portion 18.

More specifically, in FIGS. 1–7 a preferred embodiment of the thermal blanket of the present invention is illustrated which is particularly useful in covering a substantial portion of a patient's body. As best illustrated in FIGS. 6 and 7, the inflatable portion 18 includes two outer channels 30a and 30b, and six inner channels 30a–30f. In this regard, the base sheet 12 and outer sheet 14, with the baffle 34 therebetween, are secured together along the intermittent seams 36, 38 and 40, so as to define outer channels 30a and 30b above the baffle 34 and inner channels 32c and 32d below the baffle 34. Further, the base sheet 12 and outer sheet 14 are secured together along the intermittent seam 42 to form the inner channels 32a and 32b, and secured together along the intermittent seam 44 to form the inner channels 32e and 32f.

Accordingly, gas entering the inlet port 20 initially flows into, and inflates, the outer channels 30a and 30b. In the preferred embodiment, small gaps 46 in the intermittent seams 36, 38 and 40 allow some gas flow between the channels 30a and 32b and channels 30b and 32e to facilitate the rapid, and consistent, inflation of the inflatable portion 18. However, the primary fluid communication between the outer channels 30a and 30b, and the adjacent inner channels 32b and 32e is provided through primary gaps 48 provided in the seams 36 and 40 where the base sheet 12, the baffle 34, and the outer sheet 14 are not sealed together. Thus, gas entering the inlet port 20 flows down the outer channels 30a and 30b, and into the adjacent inner channels 32b and 32e so as to inflate such channels. By the time the gas flows through the primary gaps 48 into the inner channels 32b and 32e, thereby inflating such channels, the concentration of conditioned gas initially entering the inflated portion 18 through the inlet port 20 has substantially dispersed and the temperature of the gas has moderated. The gas is, in turn, communicated from the inner channels 32b and 32e, to the inner channels 32c and 32d, under the baffle 34, through the primary gaps 48 such that the inner channels 32c and 32d are inflated. Moreover, primary gaps 50 are provided in the seams 42 and 44 in order to establish fluid communication between the inner channels 32a and 32b and the inner channels 32e and 32f, respectively, thereby allowing inflation of the channels 32a and 32f.

As will be discussed further below the selective placement of the small gaps 46 in the seams 36 and 40 can be used to control how quickly the conditioned air in the outer channels 30 disperses into the inner channels 32. For example, where heated air is used to inflate the inflatable portion 18 the small gaps 46 allow a small volume of heated air in the outer channels 30 to be dispersed into the inner channels 32 to insure that there is not too great a decrease in the temperature of the air in inner channels 32. In this regard, when the gaps 46 in the seams 36 and 40 are omitted, significant cooling of the air can take place before the air is dispersed from the outer channels 30 into the inner channels 32. Whereas for certain applications this cooling may be desirable, for other applications it may be appropriate to maintain a higher temperature in the inner channels 32. Accordingly, by reducing, or eliminating the small gaps 46, fluid flow into the inner channels 32 can be limited, thereby resulting in a greater moderation of the temperature of the gas communicated from the outer channels 30 to the inner channels 32.

Figure 3:
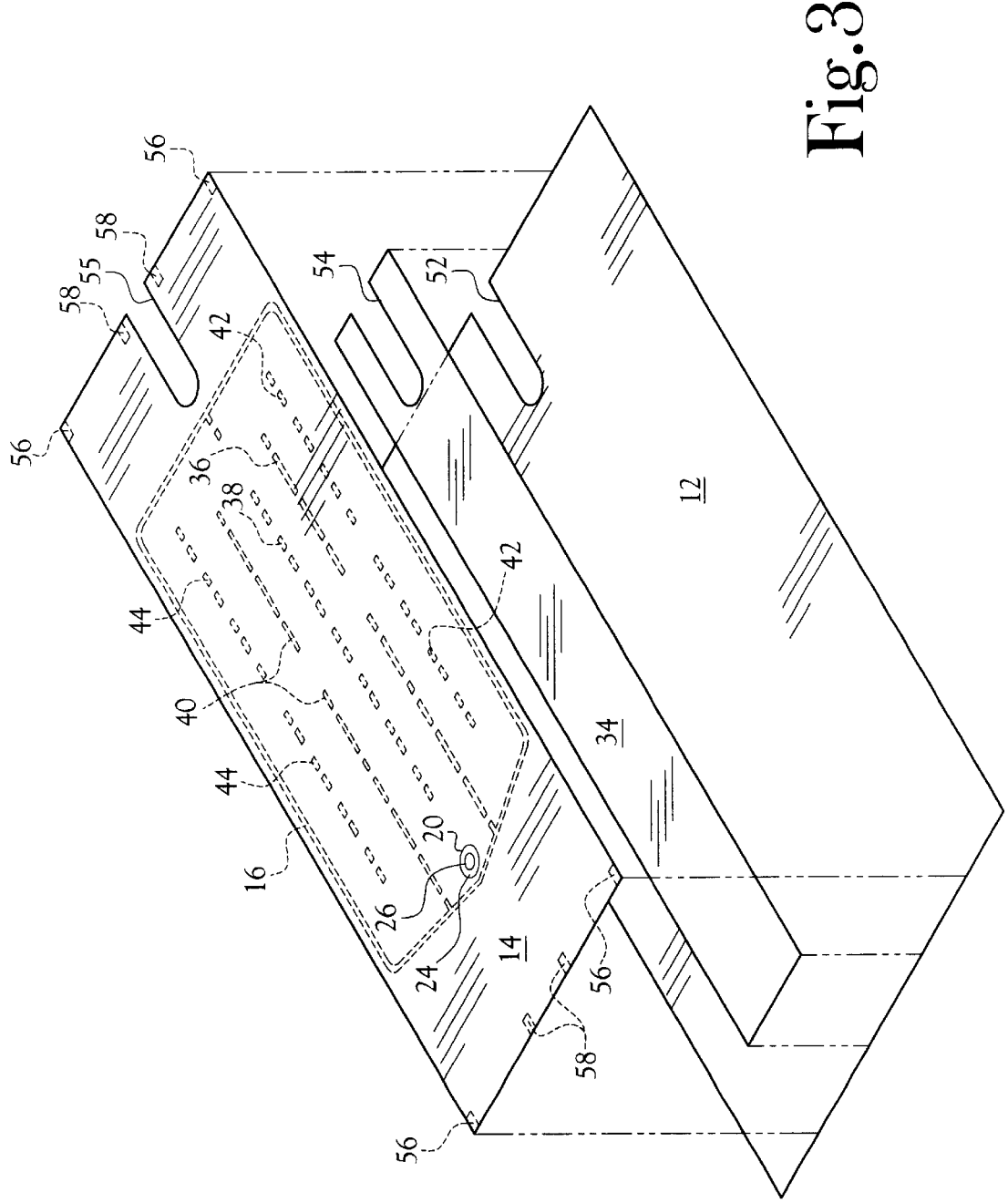
FIG. 3 is an exploded perspective view of an inflatable thermal blanket of the present invention.
Figure 4:
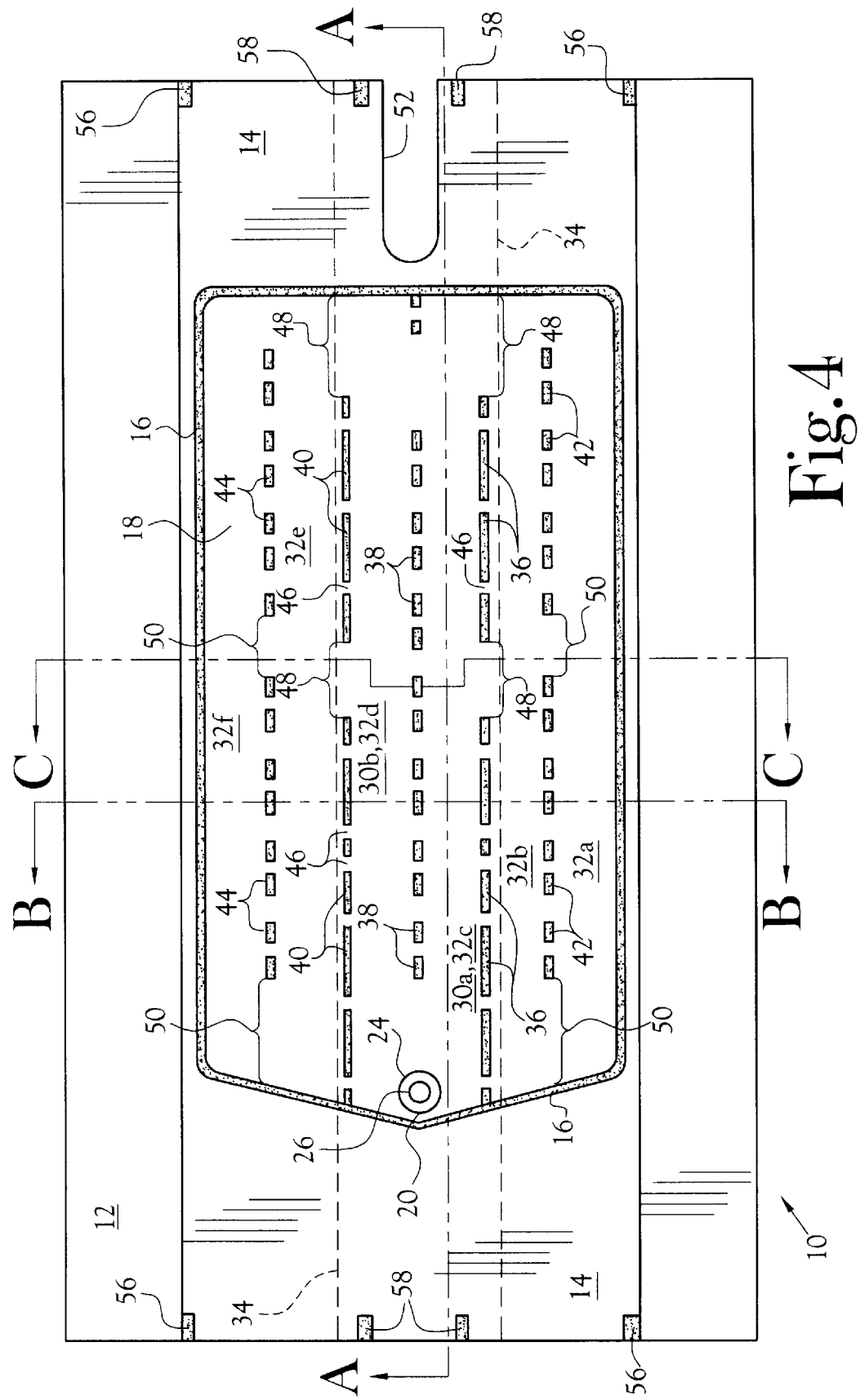
FIG. 4 is a top plan view of an inflatable thermal blanket of the present invention.

With respect to one preferred construction of the thermal blanket 10, as illustrated in FIG. 3 the base sheet 12 is substantial rectangular with a cutout portion 52 provided at one end to receive the neck of the patient. It will be noted that the base sheet 12 is substantially larger in area than the inflatable portion 18 such that when the thermal blanket 10 is in use the base sheet 12 drapes over the shoulders and feet of the patient, and over the opposite sides of the patient (see FIG. 1), in order to help retain the conditioned gas communicated to the patient beneath the base sheet 12 and around the patient. In this preferred embodiment the baffle 34 extends the length of the base sheet 12, and also defines a cutout portion 54 for receiving the neck of the patient. It will be noted in this regard that a baffle 34 having the same length as the base sheet 12 is used to facilitate manufacture of the thermal blanket 10, and it will be recognized that a baffle 34 which extends only the length of the inflatable portion 18, or along a portion of the length of the inflatable portion 18, could be used. Similarly, in order to facilitate manufacture, the outer sheet 14 extends the length of the base sheet 12, but it will be recognized that the outer sheet 14 need only be of sufficient length to form the outer wall of the inflatable portion 18. Further, the outer sheet 14 is provided with a cutout portion 55 for receiving the neck of the patient.

As discussed above, the outer sheet 14, and the baffle 34, are secured to the base sheet 12 along the various seams which form the inflatable portion 18. Additionally, the outer sheet 14 is secured to the base sheet 12, as by heat bonding, at securing points 56, and the outer sheet 14, and baffle 34, are secured to the base sheet 12, as by heat bonding, at securing points 58. Further, the reinforcing collar 24 is secured to the outer sheet 14 proximate the seam 16. In this regard, the collar 24 preferably defines an opening 26 which is approximately 2¼" in diameter, with the center of the collar 24 being preferably disposed approximately 2" from the seam 16.

Figure 8:
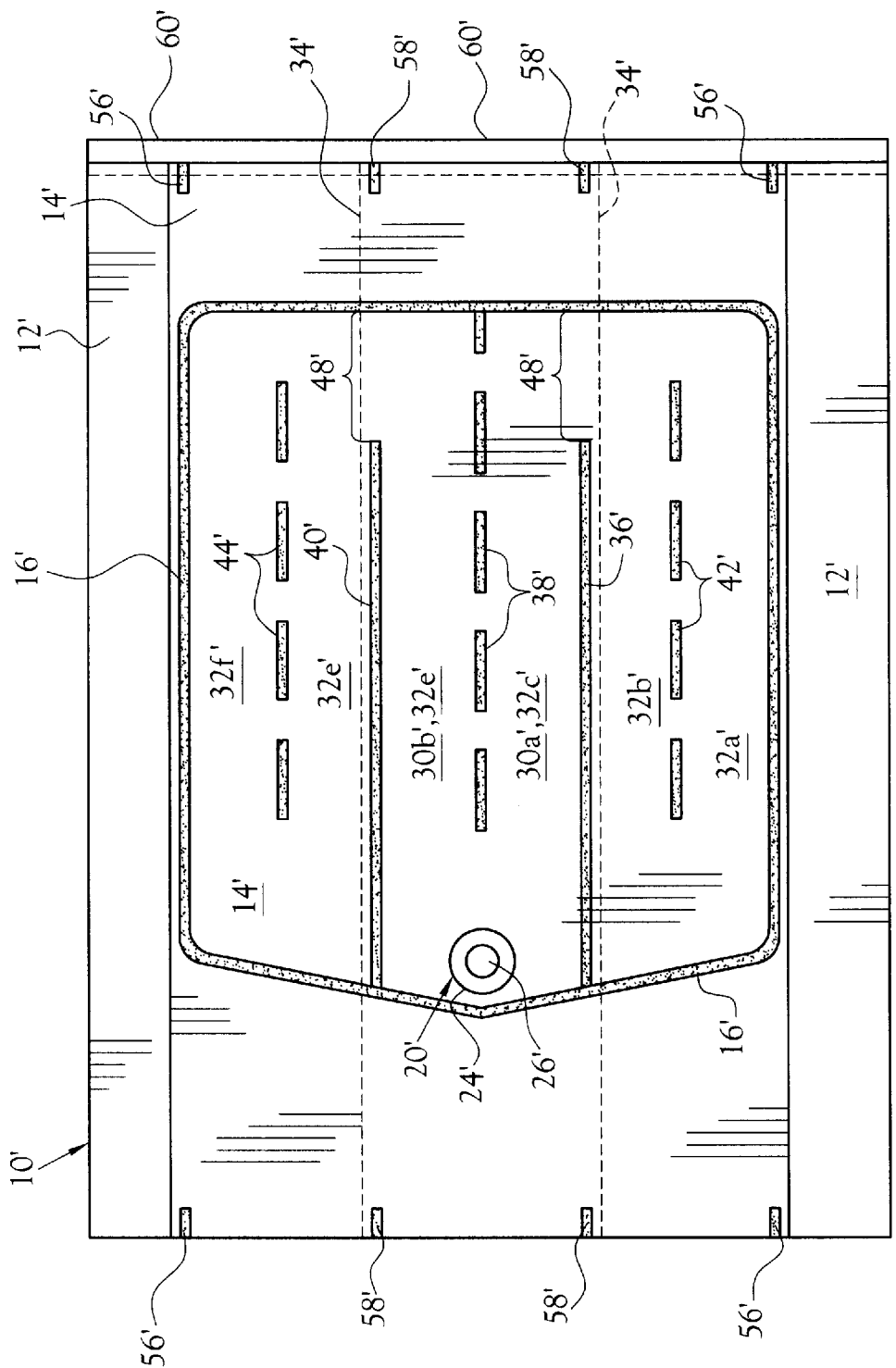
FIG. 8 is a top plan view of an alternate embodiment of an inflatable thermal blanket of the present invention.

In FIG. 8 an alternate embodiment of the thermal blanket of the present invention is disclosed at $10^1$. The thermal blanket $10^1$ is adapted to be particularly useful in bathing the lower body of a human patient in conditioned air. In this regard, instead of a cutout portion for the neck of the patient, the blanket $10^1$ is provided with a securing strip $60^1$ which extends across one edge of the base sheet $12^1$ and which is provided with an adhesive (not shown) on its inner side to allow the thermal blanket $10^1$ to be releasably secured to the patient, and/or the bed on which the patient is lying, as the inflatable portion covers the lower portion of the patient's body.

Figure 9:
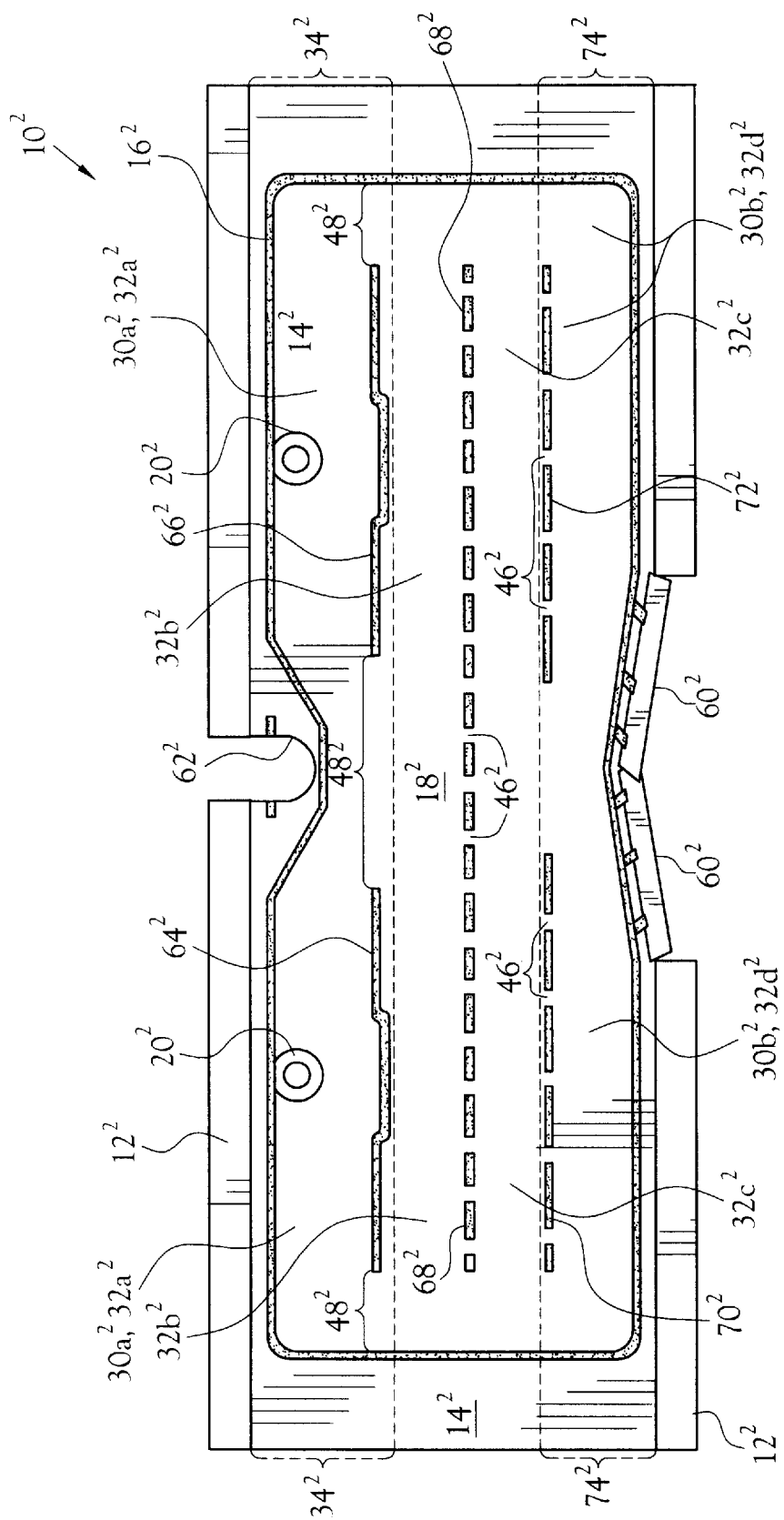
FIG. 9 is a top plan view of a second alternate embodiment of an inflatable thermal blanket of the present invention.

In FIG. 9 another alternate embodiment of the thermal blanket of the present invention is disclosed at $10^2$. The thermal blanket $10^2$ is design to cover the upper body of a patient, including the extended arms of the patient. The thermal blanket $10^2$ is provided with a cutout portion $62^2$ for receiving the neck of the patient, and is provided with securing strips $60^2$ which in the preferred embodiment are provided with an adhesive on their inner side, for releasably securing the thermal blanket $10^2$ to the patient. Accordingly, the inflatable portion $18^2$ extends laterally across the upper torso and along the length of both arms so as to allow these portions of the body to be bathed in a conditioned gas which is communicated from the inner channels $32a^2$–$32d^2$ through the base sheet $12^2$.

With respect to the construction of the thermal blanket $10^2$, the outer channel $30a^2$ is formed between the outer sheet $14^2$ and the baffle $34^2$ by the seam $16^2$ and a pair of seams $64^2$ and $66^2$. In the preferred illustrate embodiment a pair of inlet ports $20^2$ are provided which communicate with the outer channel $30a^2$, such that alternative locations are provided for connecting the thermal blanket $10^2$ to a source of pressurized gas. The inner channel $32a^2$ is formed between the baffle $34^2$ and the base sheet $12^2$ by the seams $16^2$ and the seams $64^2$ and $66^2$. Thus, it will be recognized that the inner channel $32a^2$ is disposed between the outer channel $30a^2$ and the patient, such that conditioned gas entering into the outer channel $30a^2$ through one of the inlet ports $20^2$ is not immediately communicated to the patient. In this regard, the inner channel $32b^2$ is formed between the outer sheet $14^2$ and base sheet $12^2$ by the seams $64^2$ and $66^2$, and the intermittent seam $68^2$. The inner channel $32c^2$ is formed between the outer sheet $14^2$ and the base sheet $12^2$ by the intermittent seam $68^2$ and the intermittent seams $70^2$ and $72^2$. Accordingly, conditioned gas which as been dispersed into the outer channel $30a^2$ is communicated to the inner channel $32b^2$, and is communicated from the inner channel $32b^2$ into the inner channel $32a^2$, through the primary gaps $48^2$ between the seams $64^2$ and $66^2$. Further, conditioned gas in the inner channel $32b^2$ is communicated to the inner channel $32c^2$ around the ends of the seam $68^2$ and through the small gaps $46^2$ in the seam $68^2$.

In the preferred illustrated embodiment, the thermal blanket $10^2$ is also provide with a second baffle $74^2$, and an outer channel $30b^2$ is defined between the baffle $74^2$ and the outer sheet $14^2$ by the seams 70 and 72, and the seam 16. Further, the inner channel $32d^2$ is defined below the outer channel $30b^2$. It will also be noted that the intermittent seams $70^2$ and $72^2$ have fewer small gaps $46^2$ than the intermittent seam $68^2$, thereby providing for a more restrictive gas flow into the inner channel $32d^2$. This restriction of gas flow into the inner channel $32d^2$ and the reduced volume of the inner channel $32d^2$ due to the baffle $74^2$, reduces the conditioned gas which is communicated from the inner channel $32d^2$ through the base sheet $14^2$ to the patient. Similarly, the solid seams $64^2$ and $66^2$ reduce gas flow into the inner channel $32a^2$, and the baffle $34^2$ reduces the volume of inner channel $32a^2$, thereby reducing the conditioned gas which is communicated from the inner channel $32a^2$ through the base sheet $14^2$ to the patient. As a consequence, gas flow from the inner channels $32b^2$ and $32c^2$ to the patient is greater than the gas flow from the inner channels $32a^2$ and $32d^2$. With the arms of the patient preferably being positioned beneath the more centrally located inner channels $32b^2$ and $32c^2$, this allows the flow of conditioned gas to be concentrated on the arms of the patient.

Figure 10:
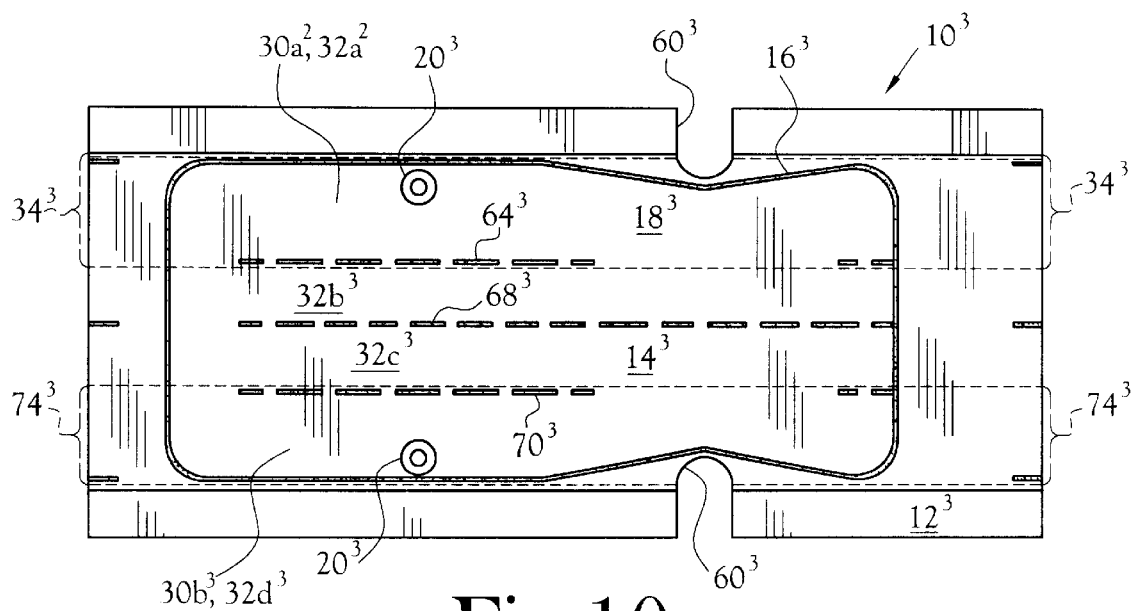
FIG. 10 is a top plan view of a third alternate embodiment of an inflatable thermal blanket of the present invention.

An alternate embodiment of the thermal blank for use in treating the upper body is illustrated at $10^3$ in FIG. 10. The thermal blanket $10^3$ is designed to cover the upper torso of a patient, and one extended arm of the patient. It will be noted that the blanket $10^3$ is provided with a pair of oppositely disposed cutout portions $60^3$ for alternatively receiving the neck of the patient such that the thermal blanket $10^3$ can be alternatively used to cover either the right or the left arm of the patient. Further, inlet ports $20^3$ are provided to alternatively access the outer channel $30a^3$ or $30b^3$ in order to facilitate the convenient connection of the blanket to a source of conditioned air.

Figure 11:
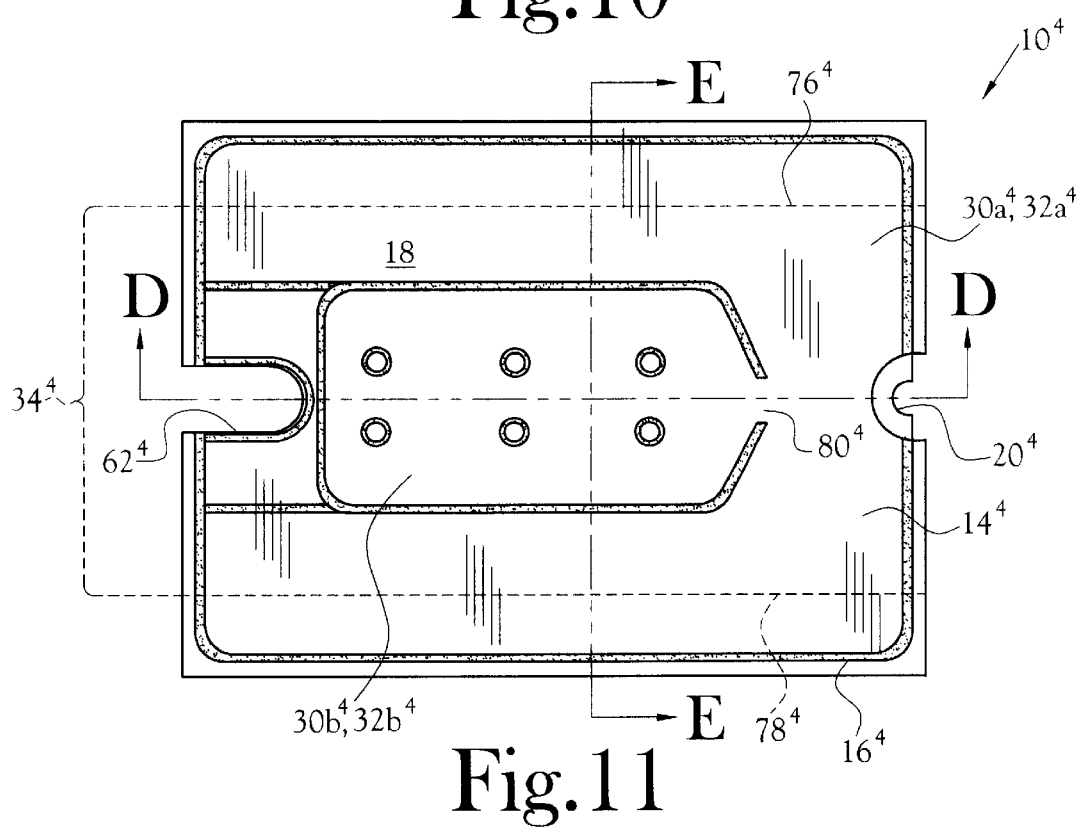
FIG. 11 is a top plan view of a forth alternate embodiment of an inflatable thermal blanket of the present invention.
Figure 11A:
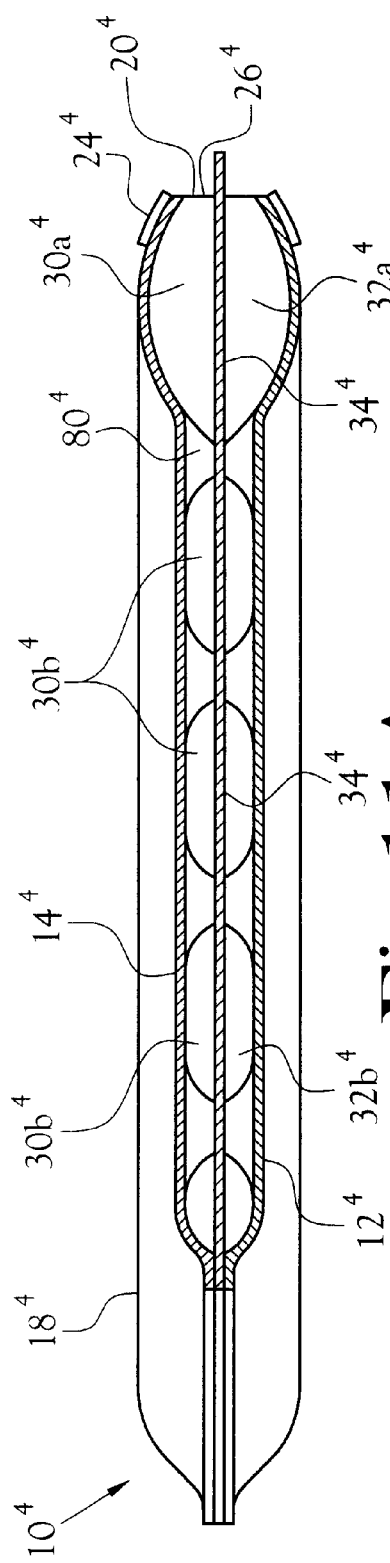
FIG. 11A is a side elevation view, in section taken at D—D of FIG. 11, of the forth alternate embodiment of the inflatable thermal blanket of the present invention.
Figure 11B:
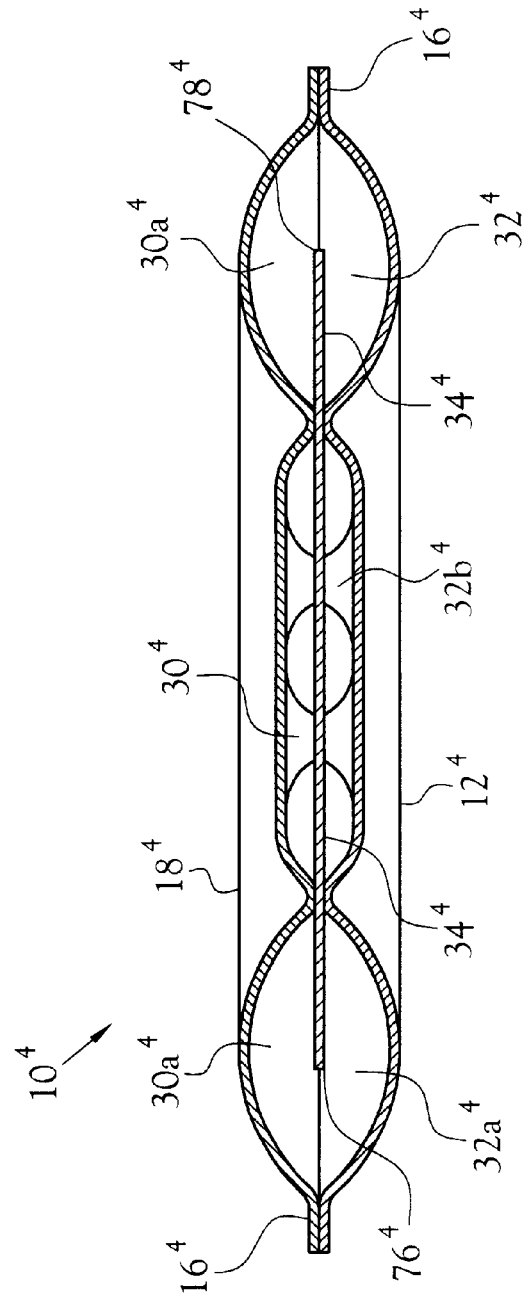
FIG. 11B is an end view, in section taken at E—E of FIG. 11, of the forth alternate embodiment the inflatable thermal blanket of the present invention.

In FIGS. 11, 11A and 11B a thermal blanket of the present invention which is configured for neonatal applications is illustrated generally at $10^4$. In this regard, the thermal blanket $10^4$ is constructed so as to limit the flow of conditioned gas communicated through the base sheet $12^4$ directly over the infant in order to avoid inappropriately rapid changes in body temperature. The thermal blanket $10^4$ defines an outer channel $30a$ which is open along the edges $76^4$ and $78^4$ of the baffle $34^4$, so as to communicate with the inner channel $32a^4$. The thermal blanket $10^4$ also defines a centrally disposed outer channel $30b^4$ and a centrally disposed inner channel $32b^4$, with the volume of the channels $30b^4$ and $32b^4$ being substantially less than the volume of the channels $30a^4$ and $32b^4$, respectively, and with air flow into the channels $30b^4$ and $32b^4$ being limited to a single narrow gap $80^4$. It will be recognized that the reduced volume of, and reduced gas flow into, the inner channel $32b^4$ results in a reduced flow of gas from the inner channel $32b^4$ to the neonatal patient, relative to the gas flow from the inner channel $32a^4$. In this regard, the infant is preferably positioned beneath the inner channel $32b^4$ where the gas flow is reduced, with the inner channel $32a^4$, which partially surrounds the infant, providing indirect gas flow to the infant.

Figure 12:
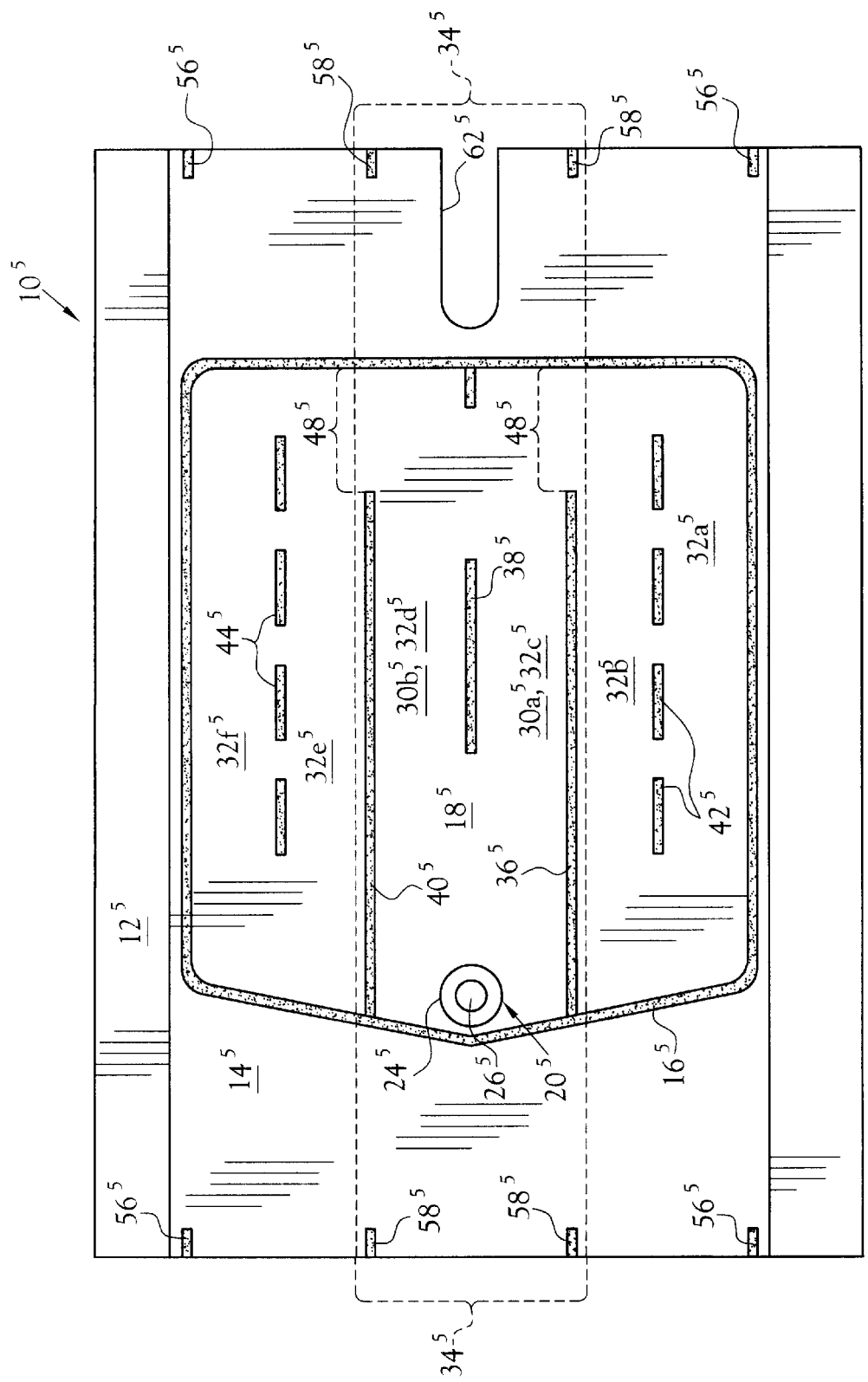
FIG. 12 is a top plan view of a fifth alternate embodiment of the inflatable thermal blanket of the present invention.

In FIG. 12 a thermal blanket of the present invention which is configured for pediatric applications is illustrated generally at $10^5$. It will be recognized that the thermal blanket $10^5$ is very similar in construction to the thermal blanket 10 discussed above. However, the overall volume and length of the outer channels $30a^5$ and $30b^5$, of the thermal blanket $10^5$ are reduced in view of the fact that the blanket is intended for use with pediatric patients. Due to the this smaller area and reduced length, the blanket $10^5$ is provided with seams $36^5$ and $40^5$ that are continuous. The absence of gaps in the seams $36^5$ and $40^5$ serves to retain the conditioned gas in the outer channels $30a^5$ and $30b^5$ over the length of such channels to allow the temperature of the gas to moderate, thereby compensating for the smaller volume and shorter length of the outer channels.

In light of the above, it will be recognized that the present invention provides a thermal blanket with significant advantages over the prior art. Prior art thermal blankets typically communicate an air flow to the patient which is uneven in temperature, and where heated air is being communicated, such blankets can generate hot spots proximate the point at which the heated air is pumped into the blanket. The unique construction of the thermal blanket of the present invention obviates such hot spots, while at the same time allowing the volume and the temperature of the air flow communicated to the patient to be controlled by the selective placement of baffles 34 and gaps 46 in the seams between outer and inner channels 30 and 32.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

Having thus described the aforementioned invention, I claim:

1. An inflatable thermal blanket for providing a conditioned gas to at least a portion of the body of a human or other animal, said thermal blanket comprising an inflatable portion for receiving the conditioned gas under pressure and for being positioned over the portion of the body, said inflatable portion being defined by a first sheet adapted for communicating the conditioned gas to the portion of the body, and a second sheet, said inflatable portion also including an inlet port for placing said inflatable portion in fluid communication with a source of conditioned gas, said inflatable portion also defining at least one outer channel communicating with said inlet port and at least one inner channel communicating with said outer channel, said inner channel being formed in part by said first sheet, said outer channel being formed at least in part by said second sheet and a baffle such that said inner channel is disposed between said outer channel and the portion of the body when said thermal blanket is in use, whereby the conditioned gas received through said inlet port is dispersed into said outer channel before being communicated to said inner channel.

2. The inflatable thermal blanket of claim 1 wherein said inflatable portion defines a plurality of said inner channels.

3. The inflatable thermal blanket of claim 2 wherein said inflatable portion defines a plurality of said outer channels.

4. The inflatable thermal blanket of claim 1 wherein said inner channel is defined by said first sheet and said baffle, whereby said baffle defines a common wall between said inner channel and said outer channel.

5. The inflatable thermal blanket of claim 1 wherein said first sheet is fabricated of a gas pervious material, whereby conditioned gas within said inner channel is communicated through said first sheet to the portion of the body.

6. The inflatable thermal blanket of claim 1 wherein said first sheet is fabricated of a substantially gas impervious material having selectively positioned openings for communicating conditioned gas within said inner channel through said first sheet to the portion of the body.

7. The inflatable thermal blanket of claim 1 wherein said first sheet is fabricated of a material having gas pervious areas and gas impervious areas, whereby the conditioned gas within said inner channel is communicated through said gas pervious areas to the portion of the body.

8. The inflatable thermal blanket of claim 4 wherein said inflatable portion defines at least one further inner channel in gas communication with said outer channel, said further inner channel being defined by said first sheet and said second sheet.

9. An inflatable thermal blanket for providing a conditioned gas to at least a portion of the body of a human or other animal, said thermal blanket comprising:

a first sheet adapted for communicating the conditioned gas to the portion of the body, a second sheet secured to said first sheet along a first seam to define an inflatable portion for receiving the conditioned gas under pressure and for being positioned over the portion of the body, said second sheet being provided with an inlet port for placing said inflatable portion in fluid communication with a source of conditioned gas, said inflatable portion defining at least a first outer channel communicating with said inlet port, said first outer channel being defined by said second sheet and a baffle disposed between said first sheet and said second sheet, said inflatable portion also defining at least a first inner channel communicating with said first outer channel, said first inner channel being defined by said first sheet and said baffle, whereby said baffle forms a common wall between said first outer channel and said first inner channel and such that said first inner channel is disposed between said first outer channel and the portion of the body when said thermal blanket is in use, whereby the conditioned gas received through said inlet port is dispersed into said first outer channel before being communicated to said first inner channel.

10. The inflatable thermal blanket of claim 9 wherein said inflatable portion defines a second inner channel in gas communication with said first outer channel, said second inner channel being defined by said first sheet and said second sheet.

11. The inflatable thermal blanket of claim 10 wherein said second inner channel communicates with said first outer channel indirectly through said first inner channel.

12. The inflatable thermal blanket of claim 9 wherein said first outer channel is formed with at least one intermittent seam securing said first sheet to said second sheet, said intermittent seam defining a plurality of gaps.

13. The inflatable thermal blanket of claim 10 wherein said inflatable portion defines a second outer channel communicating with said second inner channel, said second outer channel being defined by said second sheet and a second baffle, and wherein said inflatable portion defines a third inner channel communicating with said second inner channel, said third inner channel being defined by said second baffle and said first sheet, whereby said second baffle forms a common wall between said second outer channel and said third inner channel.

14. The inflatable thermal blanket of claim 9 wherein said inflatable portion is provided with a second inlet port for alternatively placing said inflatable portion is communication with a source of conditioned gas.

15. The inflatable thermal blanket of claim 10 wherein said first outer channel is formed with at least one intermittent seam securing said first sheet to said second sheet, said intermittent seam defining a plurality of gaps for communicating the conditioned gas to said second inner channel.

* * * * *